United States Patent [19]

Himmelmann et al.

[11] Patent Number: 4,845,024

[45] Date of Patent: Jul. 4, 1989

[54] HARDENERS FOR PROTEINS, A BINDER LAYER HARDENED THEREWITH AND A PHOTOGRAPHIC RECORDING MATERIAL CONTAINING SUCH A LAYER

[75] Inventors: Wolfgang Himmelmann; Johannes Sobel, both of Leverkusen; Hans Ohlschläger, Bergisch Gladbach; Karl-Wilhelm Schranz, Odenthal-Hahnenberg, all of Fed. Rep. of Germany

[73] Assignee: AGFA Gevaert Aktiengessellschaft, Leverkusen, Fed. Rep. of Germany

[21] Appl. No.: 83,688

[22] Filed: Aug. 7, 1987

[30] Foreign Application Priority Data

Aug. 23, 1986 [DE] Fed. Rep. of Germany ....... 3628717

[51] Int. Cl.$^4$ ................................................ G03C 1/30
[52] U.S. Cl. ..................................... 430/622; 430/623
[58] Field of Search ............................... 430/622, 623

[56] References Cited

U.S. PATENT DOCUMENTS

| | | | |
|---|---|---|---|
| 3,676,143 | 7/1972 | Himmelmann et al. | 430/623 |
| 4,323,646 | 4/1982 | Bergthaller et al. | 430/622 |
| 4,349,624 | 9/1982 | Sobel et al. | 430/622 |

*Primary Examiner*—Paul R. Michl
*Assistant Examiner*—Lee C. Wright
*Attorney, Agent, or Firm*—Connolly & Hutz

[57] ABSTRACT

Water-soluble adducts of tertiary amines with heteroaromatic bis- or polyvinyl sulfone compounds are suitable for hardening layers containing proteins as binder.

3 Claims, No Drawings

HARDENERS FOR PROTEINS, A BINDER LAYER HARDENED THEREWITH AND A PHOTOGRAPHIC RECORDING MATERIAL CONTAINING SUCH A LAYER

This invention relates to an adduct of a tertiary amine and a heteroaromatic compound containing vinyl sulfonyl groups as a hardener for proteins, to harden binder layers of which the binder contains a protein and, more particularly, to a photosensitive photographic recording material of which the protein-containing binder layers are hardened with the hardener according to the invention.

Numerous compounds have already been described as hardeners for proteins and, in particular, for gelatin. They include, for example, metal salts, such as chromium, aluminium or zirconium salts, aldehydes and halogen-containing aldehyde compounds, more especially formaldehyde, dialdehydes and mucochloric acid, 1,2- and 1,4-diketones, such as cyclohexane-1,2-dione and quinones and also chlorides or anhydrides of polybasic organic acids, such as anhydrides of tetracarboxylic acids, compounds containing several reactive vinyl groups, such as vinyl sulfones, acrylamides, compounds containing at least two readily cleavable, heterocyclic 3-membered rings, such as ethylene oxide and ethylene imine, polyfunctional methane sulfonic acid esters and bis-$\alpha$-chloroacylamido compounds.

High molecular weight hardeners, such as polyacrolein and derivatives or copolymers thereof and alginic acid derivatives, have recently become known, being used in particular as layer-limited hardeners.

However, the use of the above-mentioned compounds for photographic purposes is attended by a number of serious disadvantages. Some of these compounds are photographically active and are therefore unsuitable for hardening photographic recording materials while others adversely affect the physical properties, for example the fragility of the gelatin layers to such an extent that they cannot be used; yet others cause color formation or a change in the pH value during the hardening reaction. In addition, it is particularly important so far as the hardening of photographic layers is concerned that maximal hardening should be reached as soon as possible after drying to prevent the permeability of the material to be hardened to the developer solution from continuously changing, as in the case of mucochloric acid or formaldehyde.

Certain crosslinking agents for gelatin, such as ethylene imine compounds, also have a damaging effect on the skin so that they should not be used for physiological reasons alone.

It is also known that trichlorotriazine, hydroxydichlorotriazine and dichloroaminotriazines can be used as hardeners. The disadvantage of using hardeners such as these lies in their relatively high vapor pressure, in the release of hydrochloric acid during the hardening reaction and in the physiological effect of these compounds. Water-soluble derivatives containing carboxyl and sulfonic acid groups, obtained by reaction of cyanuric chloride with 1 mole diaminoalkyl or diaminoaryl sulfonic acid or carboxylic acid, are not attended by these disadvantages and, for this reason, have recently been proposed as hardeners. Unfortunately, their usefulness in practice is limited because, on account of their good solubility, they decompose on standing in aqueous solutions and thus very quickly lose effectiveness.

Finally, in the case of a hardener for photographic gelatin-containing layers, it is crucially important, both for production and for processing reasons, to be able to determine the onset of crosslinking within certain limits, for example through the choice of the drying temperature or the pH-value.

Compounds containing two or more acrylamide groups in the molecule, for example N,N',N''-tris-acryloyl hexahydrotriazine or methylene-bis-acrylamide, are also known as hardeners for photographic gelatin layers.

Although the hardening effect of these compounds is good after a certain time, the compounds themselves are poorly soluble in water which can cause hardening irregularities in the layer.

Particular problems arise in the increasingly common rapid processing of photographic, more especially color photographic, recording materials which imposes increased demands upon the mechanical properties and swelling behavior of the recording materials. Added to this are the difficulties which arise out of the need to produce increasingly thinner photographic layers. Attempts have been made to overcome problems such as these by using different types of hardeners. In this connection, known hardeners have either presented new difficulties or have simply proved to be unsuitable. Hardeners such as these include the many known hardeners containing vinyl sulfone groups, of which divinyl sulfone (DE-C No. 872 153) is the most well known. The toxicity of divinyl sulfone is an obstacle to its use.

DE-C-No. 1 100 942 describes aromatic vinyl sulfone compounds while DE-A-No. 1 547 733, DE-B No. 2-1 808 685 and DE-A No. 2 348 194 describe vinyl sulfonyl alkyl compounds, including those containing a heterocyclic ring.

Known vinyl sulfone compounds have proved to be unsuitable as hardeners in several respects. Either they are not sufficiently soluble in water and necessitate special measures to enable them to be used in photographic gelatin layers or, alternatively, they have an adverse effect upon the drying behavior of the layers. Others of these compounds increase the viscosity of the casting compositions to such an extent that the processing thereof to layers is affected. Another effect of known hardeners of the vinyl sulfone type, particularly in color photographic recording materials, is that photographic additives migrate from one layer to the other, resulting in changes in color and changes in the photographic properties.

Finally, reaction products obtained in reactions of compounds containing at least 3 vinyl sulfonyl groups in the molecule with compounds containing a water-soluble group and a group capable of reacting with a vinyl sulfonyl group are known as hardeners from DE-A-No. 2 635 518. The reactions in question give anionic vinyl sulfonyl compounds.

However, these compounds have disadvantages. They show significant post-hardening in gelatin-containing photographic layers, in other words they only develop their optimal effect after prolonged storage of the material. The effect of this is that the swellability of the layers in water decreases with increasing storage time, with the result that the sensitometric data of the material continuously change. Also, the addition of the known compounds to gelatin-containing silver halide emulsions, particularly at pH values around 7, is followed by an increase in viscosity with increasing digestion time which precludes error-free casting. It is also known that the crosslinking rate of gelatin is particularly high, especially in the case of the vinyl sulfonyl compounds of heteroaromatic compounds in contrast to the other hitherto known vinyl sulfones. The disadvantage here is that the heteroaromatic bis- and polyvinyl sulfone compounds are poorly soluble in water and precipitate when used in aqueous casting solutions. This gives rise to irregular hardening which, in the worst case, leads to wrinkled grain in the layer.

The object of the present invention is to provide from heteroaromatic bis- and polyvinyl sulfone compounds readily water-soluble hardeners for protein-containing binders, more especially hydrophilic binders, preferably gelatin, which have the same hardening activity as the starting compounds and which, by virtue of their solubility in water, do not show any significant post-hardening when used in photographic layers under normal climatic conditions.

According to the invention, this object is achieved by water-soluble adducts of a tertiary amine and a heteroaromatic bis- or polyvinyl sulfone.

Accordingly, the present invention relates to water-soluble adducts of a tertiary amine and a heteroaromatic bis- or polyvinyl sulfone.

The present invention also relates to hardened binder layers of which the binder contains a protein, more especially a hydrophilic protein, preferably gelatin, and which are hardened with the hardener according to the invention.

The present invention also relates to a photosensitive photographic recording material comprising at least one gelatin-containing layer hardened with a hardener, characterized in that a hardener according to the invention has been used for hardening.

The hardeners used in accordance with the invention preferably correspond to the following general formula $$Z \begin{matrix} (SO_2-CH_2-CH_2-Y)_n \\ \\ (SO_2-CH=CH_2)_m \end{matrix} \quad n.A^\ominus \quad (I)$$

in which
Y is the residue of a tertiary amine,
Z is an optionally substituted heteroaromatic ring which contains at least n+m ring-C-atoms and at east one ring—O—, —S— or —N— atom,
A is an anion, for example $Cl^\ominus$, $Br^\ominus$, $\frac{1}{2}SO_4^{2\ominus}$, $NO_3^\ominus$, $BF_4^\ominus$, $H_2PO_4^\ominus$,
n is an integer of $\geq 1$,
m is an integer of $\geq 0$ and
m+n is an integer of $\geq 2$, preferably from 2 to 5.
Suitable residues $Y^\oplus$ are, for example, -continued $R_1$, $R_2$ and $R_3$ represent $C_1$-$C_4$ alkyl, more especially methyl,
$R_4$ represents hydrogen, $C_1$-$C_4$ alkyl, $C_1$-$C_4$ hydroxyalkyl, cyano, ureido, sulfo, carboxy, 2-sulfoethyl, 2-carboxyethyl or di- $C_1$-$C_4$-alkylamino,
X is a number of 1 or 2 and
p is a number of from 2 to 1000.

Where $R_4$ is a sulfo, carboxy, sulfoethyl or carboxyethyl group, the anion $A^\ominus$ may be completely redundant or partly redundant (in the case of different residues $Y^\oplus$).

Heteroaromatic rings are understood to be maximally unsaturated 5- or 6-membered rings which contain heteroatoms and which, like benzene, contain a $\pi$-electron sextet (cf. H. BEYER, Lehrbuch der organischen Chemie, 18th Edition (1976), page 613). The heteroaromatic ring represented by Z is, for example, a triazole, thiadiazole, oxadiazole, pyridine, pyrrole, quinoxaline, thiophene, furane, pyrimidine or triazine ring. In addition to the at least two vinyl sulfonyl groups, it may optionally contain other substituents and, optionally, fused benzene rings which in turn may also be substituted. The following are examples of heteroaromatic rings (Z):

where R represents $C_1$-$C_4$ alkyl, phenyl or $C_1$-$C_4$ alkoxy. Z is preferably a 1,2,4-thiadiazole or -triazole-ring.

Adducts of tertiary amines with aliphatic or nonaromatic heterocyclic bis- or polyvinyl sulfones are known. However, compounds such as these are capable inter alia of splitting slowly in the photographic layer and hardening thereafter. Accordingly, significant post-hardening is observed, in other words the maximal crosslinking effect is only reached after days or weeks. This is undesirable so far as the production of photographic materials is concerned, because, as far as possible, they are sold without prolonged storage. In addition, the photographic properties of the material change continuously in accordance with the greater hardening.

It is surprising that, in contrast to the hitherto known compounds, the claimed adducts react extremely quickly with compounds containing amino groups, such as gelatin, with crosslinking. Although they are highly active, aqueous solutions thereof are highly stable. 30 to 50% by weight aqueous solutions may be stored for months at room temperature without any reduction in effect or polymerization being observed.

The hardeners according to the invention are prepared from the components in aqueous suspension at room temperature with addition of acid. The tertiary amines are known; the heteroaromatic compounds containing vinyl sulfone groups may be converted by reaction of heterocyclic mercapto compounds $Z\text{-}(SH)_n$ with chloroethanol or by reaction of heterocyclic polyhalogen compounds $Z\text{-}(Hal)_n$ with mercaptoethanol into the hydroxyethyl thio compounds $Z\text{-}(S\text{—}CH_2\text{—}CH_2\text{—}OH)_n$ which may be converted in known manner into the hydroxyethyl sulfonyl derivatives $Z\text{-}(SO_2\text{—}CH_2CH_2\text{—}OH)_n$ by reaction with hydrogen peroxide. On reaction with thionyl chloride for example, the hydroxyethyl sulfonyl derivatives give the chloroethyl sulfonyl compounds $Z\text{-}(SO_2\text{—}CH_2\text{—}CH_2\text{—}Cl)_n$, from which the desired products are obtained by elimination of HCl with bases, such as triethylamine.

The following compounds are mentioned by way of Example:

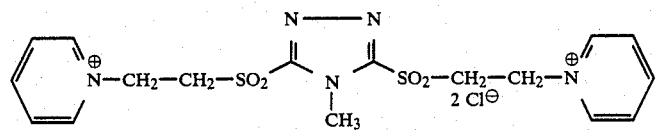

H 1

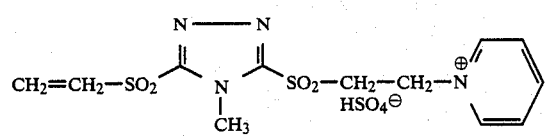

H 2

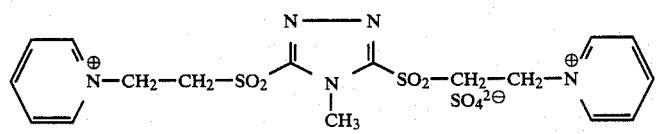

H 3

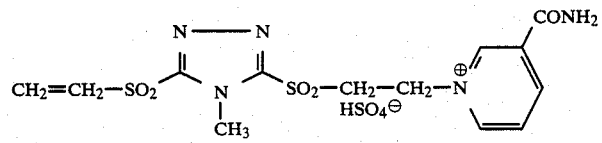

H 4

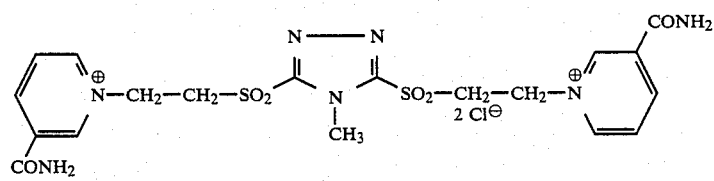

H 5

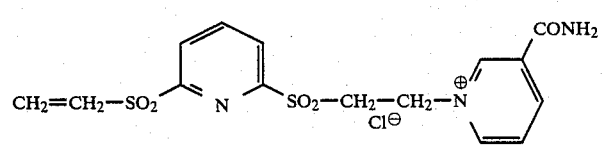

H 6

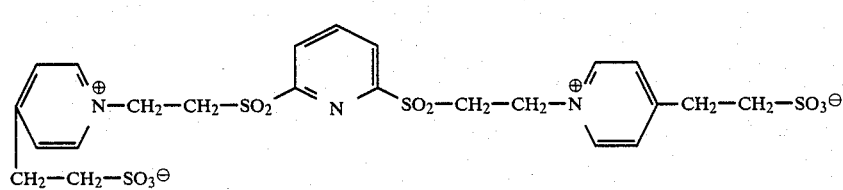

H 7

-continued
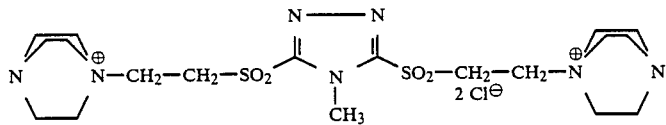
H 8
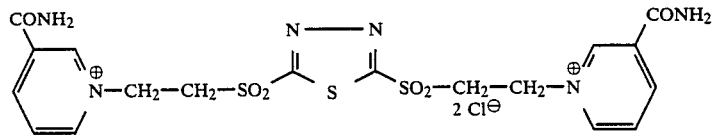
H 9
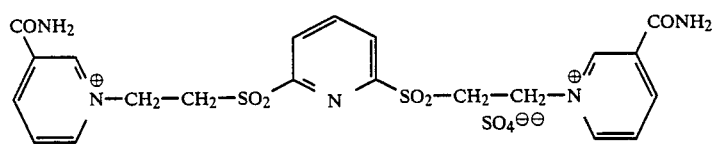
H 10
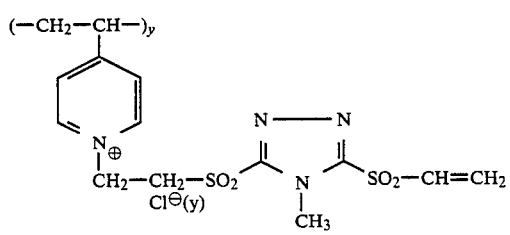
H 11
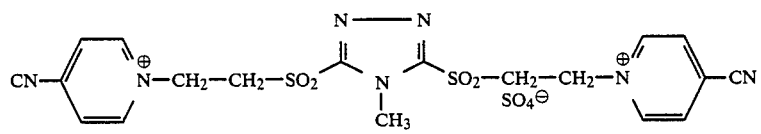
H 12
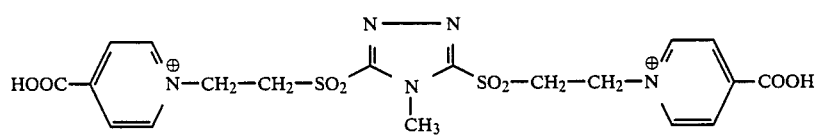
H 13
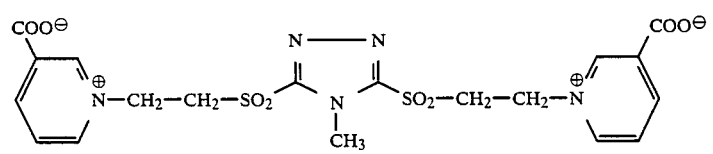
H 14
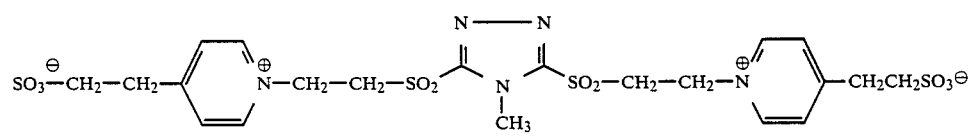
H 15
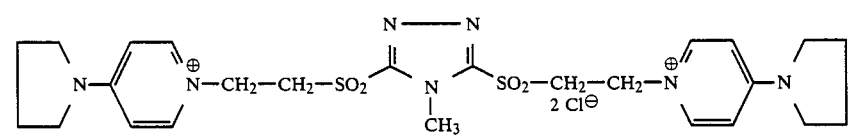
H 16
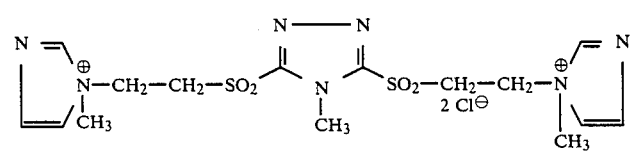
H 17

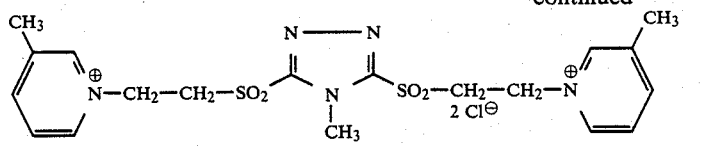

H-18

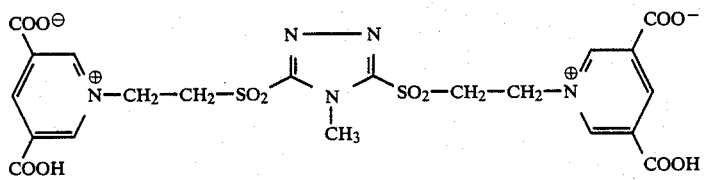

H 19

The compounds according to the invention may be prepared as follows:

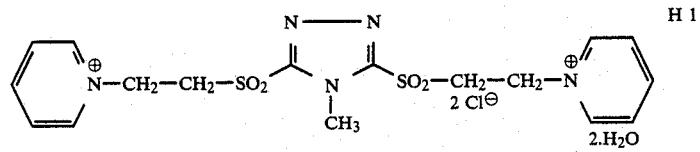

H 1

2.63 g (1/100 mole) 1-methyl-2,5-divinyl sulfonyl-1,2,4-triazole were introduced into 40 ml water. The suspension was stirred at room temperature. A solution of 1.58 g (1/50 mole) pyridine in 20 ml water adjusted to pH 5.0 with dilute hydrochloric acid was then added to the suspension. The mixture was stirred at room temperature, the pH value rising to >6.5. The pH value was kept constant at 6.5 by addition of dilute hydrochloric acid. A clear solution was formed and was concentrated by evaporation in vacuo to one fourth of its volume. The crude product was precipitated by pouring into acetone, the solvent was decanted off and the residue was washed with acetone and dried.

The compound dissolves clearly in water and melts above 200° C. 40% by weight aqueous solutions may be prepared. All other compounds may readily be prepared in the same way.

The compounds to be used in accordance with the invention generally show very good solubility in water or in a mixture of water and organic solvents. They may also be introduced in the form of a loaded latex.

The hardeners used in accordance with the invention may be added to the casting solution of a binder layer to be prepared, for example a photographic layer, either a short time before or immediately before casting, best using suitable metering systems. The compounds may also be added to an overcoating solution which, after the actual binder layer has been prepared, is applied thereto as hardening layer. The final layer sandwich may also be drawn through a solution of the hardener and is thus given the necessary quantity of hardener. Finally, in the case of multilayer materials, for example color films and color paper, the crosslinking agents according to the invention may be introduced into the layer sandwich as a whole through the intermediate layers.

The hardeners according to the invention are generally used in a quantity of from 0.01 to 15% by weight and preferably in a quantity of from 0.1 to 5% by weight, based on the dry weight of the protein, preferably the gelatin, in the coating solution. The time at which they are added to the coating solution is not critical although, in the case of silver halide emulsions, the hardener is best added after chemical ripening. pH-controlling compounds, such as bicarbonate or sodium acetate, may be applied together with the hardeners according to the invention.

The hardeners according to the invention may be used either individually or in the form of a mixture of two or more compounds according to the invention or even together with other known hardeners. Suitable additional hardeners are, for example, formaldehyde, glutaraldehyde and similar aldehyde compounds, diacetyl, cyclopentadione and similar ketone compounds, bis-(2-chloroethylurea), 2-hydroxy-4,6-dichloro-1, 3,5-triazine and other compounds containing reactive halogen, of the type described in U.S. Pat. Nos. 3,288,775, 2,732,303, GB-A-Nos. 974 723 and 1 167 207; divinyl sulfone, 5-acetyl-1,3-diacryloyl hexahydro-1,3,5-triazine and other compounds containing a reactive olefin bond of the type described in U.S. Pat. Nos. 3,635,718, 3,232,763 and GB-A-No. 994 869; N-hydroxymethyl phthalimide and other N-methylol compounds of the type described in U.S. Pat. No. 2,732,316 and 2,586,168; isocyanates of the type described in U.S. Pat. No. 3,103,437; aziridine compounds of the type described in U.S. Pat. Nos. 3,017,280 and 2,983,611; acid derivatives of the type described in U.S. Pat. Nos. 2,725,294 and in 2,725,295; compounds of the carbodiimide type as described in U.S. Pat. No. 3,100,704; carbamoyl pyridinium salts of the type described in DE-A-Nos. 22 25 230 and in 24 39 551; carbamoyloxypyridinium compounds of the type described in DE-A-No. 2 408 814, compounds containing a phosphorus-halogen bond of the type described in JP-A-No. 113 928/83, N-carbonyloximide compounds of the type described in JP-A- No. 43 353/81, N-sulfonyloxyimido compounds of the type described in U.S. Pat. No. 4,111,926, dihydroquinoline compounds of the type described in U.S. Pat. No. 4,013,468, 2- sulfonyloxypyridinium salts of the type described in JP-A-No. 110 762/81, formamidinium salts of the type described in EP-A-No. 0 162 308, compounds containing two or more N-acyloxyimino groups in the molecule of the type described in U.S. Pat. No. 4,052,373, epoxy compounds of the type described in U.S. Pat. No. 3,091,537; compounds of the isoxazole type described in U.S. Pat. Nos. 3,321,313 and 3,543,292; halogen carboxyaldehydes, such as mucochloric acid; dioxane derivatives, such as dihydroxydioxane and dichlorodioxane; and inorganic hardeners, such as chrome alum and zirconium sulfate. In addition to the hardeners mentioned above, the hardeners according to the invention may be used together with precursors of the compounds described above, for example with alkali metal bisulfite-aldehyde adducts, methylol derivatives of hydantoin and primary fatty nitroalcohols, etc. Where they are used together with other hardeners, the hardeners according to the invention may be used in quantities selected as required, depending on the objective and the desired effect.

The protein of the hardened binder layer according to the invention generally serves as binder for reactive or non-reactive substances dispersed therein, for example dyes or compounds which experience a change, for example during exposure or subsequent processing, and in doing so develop a certain activity. The binder layers hardened in accordance with the invention may be present, for example, in the form of colored coatings. The protein hardened in accordance with the invention is also suitable as a binder for diagnostic purposes. For example, dry chemical test materials, also known as test strips, may be provided with a protein layer hardened in accordance with the invention, in which the reagents required for the particular specific detection reaction, such as enzymes, co-enzymes, dye-producing agents and the like, are incorporated. The hardened protein may also be used in photographic or thermophotographic single-layer or multilayer recording materials, for example as a binder for silver halide, color couplers and other photographically active substances.

In the context of the invention, photographic layers are understood quite generally to be any of the layers which are used in photographic recording materials, for example photosensitive silver halide emulsion layers, protective layers, filter layers, antihalo layers, backing layers, image-receiving layers or, quite generally, photographic auxiliary layers.

Examples of photosensitive gelatin-containing emulsion layers, for the hardening of which the hardeners according to the invention are eminently suitable, are layers of the type which contain photosensitive compounds, particularly silver halide, optionally in spectrally sensitized form. Layers such as these are normally present in photographic recording materials for any of the various photographic black-and-white or color processes, such as negative, positive, diffusion transfer or printing processes. The hardeners according to the invention have proved to be particularly advantageous for the hardening of photographic layer combinations intended for carrying out color photographic processes, for example those which contain color couplers or other dye-producing compounds or those which are intended for treatment with solutions containing color couplers.

The effect of the hardeners according to the invention is not impaired by any of the usual photographic additives. The hardeners according to the invention are also unaffected by photographically active substances, such as water-soluble or emulsified water-insoluble dye components, stabilizers, sensitizers and the like. They also have no adverse effect on the photosensitive silver halide emulsion.

As photosensitive constituent the emulsions may contain any silver halide which as the halide may contain chloride, bromide and iodide or mixtures thereof. For example, 0 to 12 mole % of the halide of at least one layer may consist of iodide, 0 to 50 mole % of chloride and 50 to 100 mole % of bromide. The crystals are predominantly compact crystals which are, for example, cubic or octahedral or have transitional forms. They may be characterized by the fact that they mostly have a thickness of greater than 0.2 $\mu$m. The average ratio of diameter to thickness is preferably less than 8:1, the diameter of a crystal being defined as the diameter of a circle with an area corresponding to the projected area of the crystal. However, the layers may even contain substantially tablet-form silver halide crystals in which the ratio of diameter to thickness is greater than 8:1. Reference may be made in this connection to Research Disclosure 22 534 (January 1983). The emulsions may be heterodisperse or even monodisperse emulsions which preferably have a mean grain size of from 0.3 $\mu$m to 1.2 $\mu$m. The silver halide grains may even have a layered grain structure. In addition to the silver halide, the emulsions may also contain organic silver salts, for example silver benzotriazolate or silver behenate.

The emulsions may be chemically and/or spectrally sensitized in the usual way. They may also be stabilized by suitable additives. Suitable chemical sensitizers, spectral sensitizing dyes and stabilizers are described, for example, in Research Disclosure 17643, cf. in particular Chapters III, IV and VI.

The binder principally used in accordance with the invention is a protein-like binder, more especially gelatin. The main feature of this binder is the presence of functional groups with which the vinyl sulfonyl groups of the hardener according to the invention are capable of reacting, more especially amino groups. The protein-like binder may be partly modified, for example by partial acylation, or may be replaced by other natural or synthetic binders providing adequate reactivity with the hardener according to the invention is maintained. Casting aids and plasticizers may be used. Reference is made in this connection to Research Disclosure 17643, particularly Chapters IX, XI and XII.

The binder layer may contain photographically inert particles of inorganic or organic character, for example as delustrants or as so-called spacers. Particles such as these may consist of an organic polymer, cf. for example DE-A-Nos. 33 31 542, 34 24 893 and Research Disclosure 17643, Chapter XVI.

Color photographic recording materials normally contain at least one silver halide emulsion layer for recording light of each of the three spectral regions, red, green and blue. To this end, the photosensitive layers are spectrally sensitized in known manner by suitable sensitizing dyes. Blue-sensitive silver halide emulsion layers do not necessarily have to contain a spectral sensitizer because, in many cases, the natural sensitivity of the silver halide is sufficient for recording blue light.

Each of the photosensitive layers mentioned may consist of a single layer or, in known manner, for example as in the so-called double layer arrangement, may also comprise two or more partial silver halide emulsion layers (DE-C-No. 1 121 470). Normally, red-sensitive silver halide emulsion layers are arranged nearer the layer support than green-sensitive silver halide emulsion layers which in turn are arranged nearer than blue-sensitive emulsion layers, a non-photosensitive yellow filter layer generally being arranged between the green-sensitive layers and blue-sensitive layers. However, other arrangements are also possible. A non-photosensitive intermediate layer, which may contain agents to prevent the unwanted diffusion of developer oxidation products, is generally arranged between layers of different spectral sensitivity. Where several silver halide emulsion layers of the same spectral sensitivity are present they, may be arranged immediately adjacent one another or in such a way that a photosensitive layer of different spectral sensitivity is present between them (DE-A-Nos. 1 958 709, 2 530 645, 2 622 922).

Color photographic recording materials for the production of multicolor images normally contain dye-producing compounds, for example color couplers, for producing the different component dye images cyan, magenta and yellow in spatial and spectral association with the silver halide emulsion layers of different spectral sensitivity.

In the context of the invention, spatial association means that the color coupler is present in such a spatial relationship to the silver halide emulsion layer that the two are capable of interacting in such a way as to allow imagewise accordance between the silver image formed during development and the dye image produced from the color coupler. This result is generally achieved by the fact that the color coupler is contained in the silver halide emulsion layer itself or in an adjacent, optionally non-photosensitive binder layer.

By spectral association is meant that the spectral sensitivity of each of the photosensitive silver halide emulsion layers and the color of the component dye image produced from the particular spatially associated color coupler bear a certain relationship to one another, a component dye image relating to another color (generally for example the colors cyan, magenta or yellow in that order) being associated with each of the spectral sensitivities (red, green, blue).

One or more color couplers may be associated with each of the differently spectrally sensitized silver halide emulsion layers. Where several silver halide emulsion layers of the same spectral sensitivity are present, each of them may contain a color coupler, the color couplers in question not necessarily having to be the same. They are merely required to produce at least substantially the same color during color development, normally a color which is complementary to the color of the light to which the silver halide emulsion layers in question are predominantly sensitive.

In preferred embodiments, therefore, at least one non-diffusing color coupler for producing the cyan component dye image, generally a coupler of the phenol or α-naphthol type, is associated with red-sensitive silver halide emulsion layers. At least one non-diffusing color coupler for producing the magenta component dye image, normally a color coupler of the 5-pyrazolone, indazolone or pyrazolo-azole type, is associated with green-sensitive silver halide emulsion layers. Finally, at least one non-diffusing color coupler for producing the yellow component dye image, generally a color coupler containing an open-chain ketomethylene group, is associated with blue-sensitive silver halide emulsion layers. Color couplers of this type are known in large numbers and are described in a number of patent specifications. Reference is made here for example to the publications "Farbkuppler (Color Couplers)" by W. PELZ in "Mitteilungen aus den Forschungslaboratorien der Agfa, Leverkusen/Munchen", Vol. III, page 111 (1961) and by K. VENKATARAMAN in "The Chemistry of Synthetic Dyes", Vol. 4, 341 to 387, Academic Press (1971), and to Research Disclosure 17643, Chapter VIII.

The color couplers according to the invention may be both typical 4-equivalent couplers and also 2-equivalent couplers in which a smaller quantity of silver halide is required for dye production. 2-equivalent couplers are known to be derived from the 4-equivalent couplers in that they contain in the coupling position a substituent which is eliminated during the coupling reaction. 2-equivalent couplers include both those which are substantially colorless and also those which have a strong color of their own which either disappears during the color coupling reaction or is replaced by the color of the image dye produced. Couplers of the latter type may also be additionally present in the photosensitive silver halide emulsion layers where they serve as masking couplers for compensating the unwanted secondary densities of the image dyes. However, 2-equivalent couplers also include the known white couplers, although couplers such as these do not produce a dye on reaction with color developer oxidation products. 2-equivalent couplers also include couplers which contain in the coupling position a releasable group which is released on reaction with color developer oxidation products and, in the process, develops a certain, desirable photographic activity, for example as a development inhibitor or accelerator, either drectly or after one or more groups have been split off from the radical released (cf. for example DE-A-Nos. 27 03 145, 28 55 697, 05 026, 33 19 428). Examples of 2-equivalent couplers such as these are the known DIR couplers and also DAR and FAR couplers. The releasable group may also be a ballast group, so that coupling products, for example dyes, which are diffusible or which at least show slight or limited mobility, are obtained during the reaction with color developer oxidation products.

By slight or limited mobility is meant a mobility which is gauged in such a way that the contours of the discrete dye patches formed during chromogenic development blend and merge with one another. This degree of mobility should be distinguished on the hand from the usual case of complete immobility in photographic layers which, in conventional photographic recording materials, is required for the color couplers or rather for the dyes produced therefrom in order to obtain maximal definition and, on the other hand, from the case of total mobility of the dyes as required, for example, in dye diffusion processes. The last-mentioned dyes generally have at least one group which makes them soluble in alkaline medium. The extent of the slight mobility required in accordance with the invention may be controlled by varying substituents in order, for example, specifically to influence solubility in the organic medium of the oil former or affinity for the binder matrix.

High molecular weight color couplers are described, for example,in DE-C-No. 1 297 417, DE-A-Nos. 24 07 569, 31 48 125, 32 17 200, 33 20 079, 33 24 932, 33 31 743, 33 40 376, EP-A-No. 27 284, U.S. Pat. No. 4,080,211. The high molecular weight color couplers are generally produced by polymerization of ethylenically unsaturated monomeric color couplers. However, they may also be obtained by polyaddition or polycondensation.

The binder layers may contain filter and antihalo dyes, for example oxonol dyes of the type described in U.S. Pat. Nos. 2,274,782, 2,611,696, FR-A-No. 1 290 430, GB-A-No. 1 177 429, DE-A-Nos. 1 572 256, 22 59 746, 23 21 470, U.S. Pat. No. 3,984,246, styryl dyes of the type described in U.S. Pat. No. 2,036,546, DE-B-

Nos. 1 014 430, 1 028 425, 1 112 801, 1 104 335, azo dyes of the type described in DE-B-Nos. 1 103 135, 1 182 067, GB-A-No. 1 122 298, DE-A-No. 1 547 646, triphenylmethane dyes of the type described in DE-B-No. 1 008 114, anthraquinone dyes of the type described in U.S. Pat No. 2,865,752 or merocyanines of the type described in GB-A-No. 1 030 392 or U.S. Pat. No. 4,366,221. Reference may also be made to Research Disclosure 17643, Chapter VIII.

The binder layers may contain UV absorbers, optionally even in high molecular weight form. Reference is made in this connection to DE-A-Nos. 35 01 722, 35 05 423, 35 31 383, EP-A-Nos. 0 027 242, 0 057 160 and to Research Disclosure 17643, Chapter VIII, and Research Disclosure 18716, more especially page 650, left-hand column.

The binder layers may contain dye stabilizers of the type described in DE-A-No. 35 01 722, EP-A-Nos. 0 011 051, 0 026 742, 0 069 070, 0 098 241, 0 114 028, 0 114 29 and in Research Disclosure 17643, Chapter VII, more especially Section J.

The binder layers may contain optical brighteners or fluorescent whitening agents, cf, for example Research Disclosure 17643, Chapter V.

The binder layers contain so-called scavenger compounds, i.e. compounds which are capable of reacting with developer oxidation products and preventing them from diffusing into adjacent layers, cf. for example EP-A-Nos. 0 098 072, 0 124 877, 0 069 070, U.S. Pat. No. 4,366,226 EP-A-No. 0 125 522 and also Research Disclosure 17643, more especially Chapter VII, Section I, Research Disclosure 17842 (February 1979) and Research Disclosure 18716 (November 1979), more especially page 650.

The compounds to be introduced may be added by initially preparing a solution or a dispersate of the compound in question and then adding it to the casting solution. The solvent or dispersant used is determined by the particular requirements. Hydrophobic compounds may be introduced into the casting solution using high-boiling solvents, so-called oil formers. Corresponding methods are described, for example, in U.S. Pat. No. 2,322,027, in DE-A-No. 1 722 192 and in EP-A-No. 0 043 037. The compounds may also be introduced into the casting solution in the form of charged latices, cf. for example DE-A-Nos. 25 41 230, 25 41 274, 28 35 856, EP-A-Nos. 0 014 921, 0 069 671, 0 130 115, U.S. Pat. No. 4,291,113.

The binder layers may also contain agents which are capable of reacting with aldehydes, particularly formaldehyde, so-called aldehyde scavengers, or compounds which are capable of protecting other compounds incorporated, more especially other color couplers, against the damaging effect of aldehydes. Aldehyde scavengers of the type in question include, for example, N,N'-ethylene urea, 2,3-dihydroxynaphthalene or dimedone, cf. for example DE-A-No. 1 772 816.

For processing, the recording material according to the invention is developed with a color developer compound. Suitable color developer compounds are any developer compounds which are capable of reacting in the form of their oxidation product with color couplers to form azomethine or indoquinone dyes. Suitable color developer compounds are aromatic compounds containing at least one primary amino group of the p-phenylenediamine type, for example N,N-dialkyl-p-phenylenediamines, such as N,N-diethyl-p-phenylenediamine, 1-(N-ethyl-N-methylsulfonamido-ethyl)-3-methyl-p-phenylenediamine, 1-(N-ethyl-N-hydroxy-ethyl-3-methyl-p-phenylenediamine and 1-(N-ethyl-N-methoxy-ethyl)-3-methyl-p-phenylenediamine. Other suitable color developers are described, for example, in J. Amer. Chem. Soc. 73, 3106 (1951) and in G. Haist, Modern Photographic Processing, 1979, John Wiley and Sons, New York, pages 545 et seq.

After color development, the material is bleached and fixed in the usual way. Bleaching and fixing may be carried out separately from one another or even in conjunction with one another. Suitable bleaching agents are the usual compounds, for example $Fe^{3+}$ salts and $Fe^{3+}$ complex salts, such as ferricyanides, dichromates, water-soluble cobalt complexes, etc. Particularly preferred bleaching agents are iron(III) complexes of aminopolycarboxylic acids, in particular for example ethylenediamine tetra-acetic acid, nitrilotriacetic acid, iminodiacetic acid, N-hydroxyethyl ethylenediamine triacetic acid, alkyliminodicarboxylic acids and of corresponding phosphonic acids. Persulfates are also suitable bleaching agents.

Favorable results may be obtained where an aqueous final bath containing little or no formaldehyde is used.

EXAMPLE 1

The following layers were successively applied to a cellulose triacetate layer support provided with an adhesive layer (the quantities indicated are based on 1 $m_2$).

1. An antihalo layer containing 4 g gelatin and 0.7 g colloidal black silver, 2. a 6 μm thick red-sensitive layer containing 35 mmoles silver bromide iodide (5 mole % AgI), 4 mmoles of a cyan coupler corresponding to the following formula

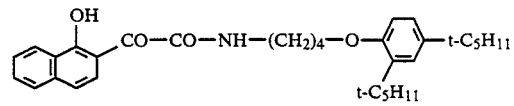

and 6 g gelatin, 3. a 0.5 μm thick gelatin intermediate layer, 4. a 6 μm thick green-sensitive layer containing 30 mmoles silver bromide iodide (5 mole % AgI), 1.3 mmoles of a magenta coupler corresponding to the following formula

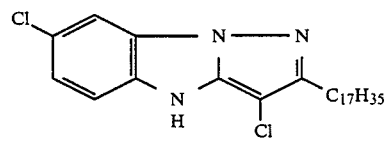

and 5 g gelatin, 5. a 0.5 μm thick gelatin intermediate layer, 6. a yellow filter layer containing 1.5 g gelatin and 0.2 g colloidal yellow silver, 7. a 6 μm thick blue-sensitive layer containing 13 mmoles silver bromide iodide (5 mole % AgI), 2 mmoles of a yellow coupler corresponding to the following formula

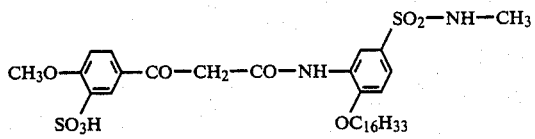

and 5 g gelatin and
8. a 1 μm thick gelatin layer.

The multilayer material was then dried.

The photographic film thus produced was used in the following as comparison material.

The production of the film was repeated, one of the hardeners H-5 and H-1 according to the invention and, for comparison, the comparison hardener C-1 being added to the individual layers per film sample in a quantity of 0.0075 mole/100 g gelatin.

The comparison hardener has the following formula:

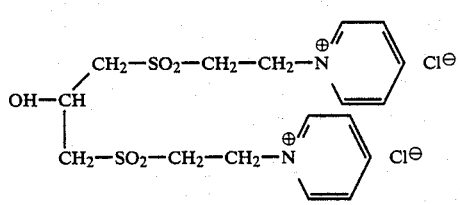

The samples hardened as described above were then tested by the methods described hereinafter. The results are shown in Table 1.

The hardening of the photographic layers was determined through the melting point of the layers which may be determined as follows:

The multilayer material cast on a support is semi-immersed in water continuously heated to 100° C. The temperature at which the layer runs off the support (streak formation) is called the melting point or separation point. In this measuring process, unhardened protein or color layers show no increase in melting point. Under these conditions, the melting point or separation point is 30° to 35° C.

To determine water uptake, the test specimen is developed as a black sheet in a conventional color development process and, after the final bath, is weighed after surplus water has been stripped off. The sample was then dried and reweighed. The weight difference, converted from the surface area of the test specimen to 1 m², represents the water uptake per m².

Swelling was gravimetrically measured after treatment of a sample strip for 10 minutes in distilled water at 22° C. It is characterized by the swelling factor:

$$\frac{\text{Layer weight, wet}}{\text{Layer weight, dry}} = \text{swelling factor}$$

To determine wet scratch resistance, a metal point of defined size was guided over the wet layer and loaded with increasing weight. The wet scratch resistance is expressed as the weight at which the point leaves a visible scratch mark on the layer. A high weight corresponds to a high wet scratch resistance.

The wrinkled grain is assessed with a magnifying glass, (8×) after swelling (for 10 minutes) in water at 22° C. Uneven hardening of the gelatin-containing layers caused by the insolubility of the hardener in aqueous solution leads to locally different vertical and horizontal swelling and hence to an irregular surface (wrinkled grain).

TABLE 1

| Sample no. | Hardener | Storage for 36 h at 57° C./ 34% rel. humidity | | | Storage for 3 d at 23° C. in the absence of moisture | Storage for 7 d at 36° C./ 80% rel. humidity | | | |
|---|---|---|---|---|---|---|---|---|---|
| | | Melting point of layer [°C.] | Swelling factor | Wet scratch resistance [N] | Melting point of layer [°C.] | Melting point of layer [°C.] | Swelling factor | Wet scratch resistance [N] | Wrinkled grain |
| 1 | — | 40 | 6–8 | — | 40 | 40 | 6–8 | — | — |
| 2 | H-5 | 100 | 2.6 | 5.0 | 100 | 100 | 2.4 | 6.0 | — |
| 3 | H-1 | 100 | 3.0 | 3.5 | 100 | 100 | 2.8 | 4.5 | — |
| 4 | C-1 | 100 | 4.8 | <2.0 | 40 | 100 | 4.5 | <2.5 | — |

It can be seen from Table 1 that the overall properties of the compounds H 1 and H 5 according to the invention are better than those of comparison compound C 1.

EXAMPLE 2

A color reflection material was prepared by successively applying the following layers to a polyethylene-lined paper support provided with an adhesive layer, the emulsion layers containing the usual additions of wetting agents, stabilizers etc.:

1. as bottom layer a 4 μm thick blue-sensitive silver halide emulsion layer containing per kg emulsion 25.4 g silver chloride bromide (12 mole % AgCl), 80 g gelatin and 34 g of the following yellow component

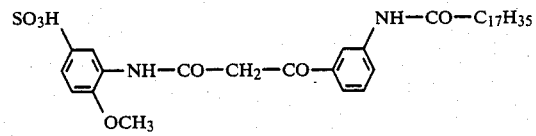

2. as intermediate layer, a 1 μm thick gelatin layer,
3. as middle layer, a 4 μm thick green-sensitive silver halide emulsion layer containing per kg emulsion 22 g silver chloride bromide (77 mole % AgCl), 80 g gelatin and 13 g of the following magenta component

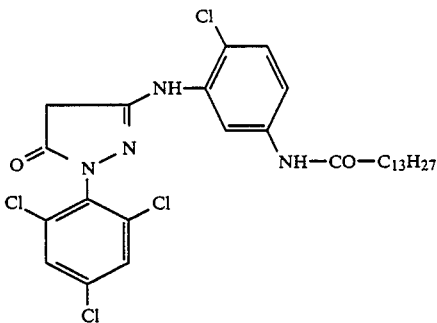

4. a 1 μm thick intermediate layer as described in 2, 5. as top layer, a 4 μm thick red-sensitive silver halide emulsion layer containing per kg emulsion 23 g silver chloride bromide (80 mole % AgCl), 80 g gelatin and 15.6 g of the following cyan component

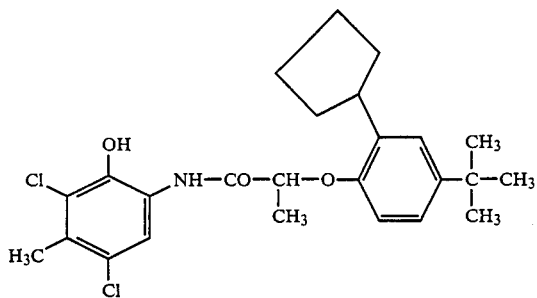

6. a 1 μm thick protective layer of gelatin.

Aqueous solutions of compounds H-1, H-5 and the comparison hardener C-2 (1/200 mole per 100 ml in each case) were applied to the dried multilayer material, followed by drying. The layers were inspected for crosslinking after storage under normal conditions and under tropical conditions.

It can be seen from Table 2 that the comparison hardener C 2 hardens considerably more slowly than the hardeners according to the invention.

The entire multilayer material is very firmly hardened after only normal storage by the diffusing compounds according to the invention. The layers have satisfactory interfaces with no wrinkled grain.

The comparison compound C 2 only hardens after storage under tropical conditions. As a result, significant posthardening occurs during storage so that the photographic properties change with time (reduction in gradation, reduction in maximal density).

With the hardeners according to the invention, no reduction is observed in the intensity of hardening as a function of the distance from the uppermost layer (hardener-containing coating).

After color photographic processing in standard processing baths, layers having comparable photographic values (sensitivity, fogging, gradation) are obtained. When used in this form, the hardening system according to the invention is inert to the emulsion and to the color couplers.

EXAMPLE 3

A gelatin-containing AgBr/AgI emulsion with corresponding sensitization and stabilization by a 2 μm thick protective layer was applied to a cellulose triacetate support. The multilayer material was overcoated with an overcoating solution containing 1.5% by weight gelatin, 0.01% by weight wetting agent corresponding to the following formula $C_8F_{17}SO_3^\ominus N^\oplus(C_2H_5)_4$ and the hardener in such a quantity that 0.08 mole hardener acted on 100 g gelatin.

The layers were dried and then stored for 3 days at room temperature in the absence of moisture and for 3 days at 57° C./34% relative air humidity.

The layer melting points, the swelling factor in water at 22° C. and wet scratch resistance in a black-and-white developer at 38° C. were then determined.

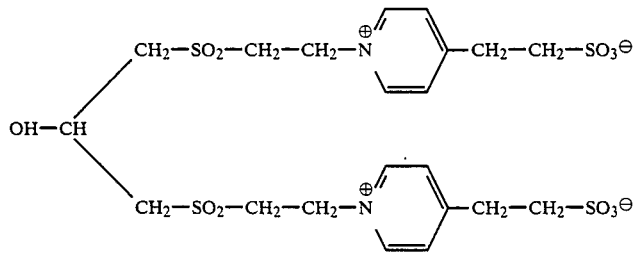

The results are shown in Table 2.

TABLE 2

| Sample no. | Hardener | Storage for 36 h at 57° C./ 34% rel. humidity | | | Storage for 3 d at 23° C. in the absence of moisture | Storage for 7 d at 36° C./ 80% rel. humidity | | |
|---|---|---|---|---|---|---|---|---|
| | | Melting point of layer [°C.] | Swelling factor | Wet scratch resistance [N] | Melting point of layer [°C.] | Melting point of layer [°C.] | Swelling factor | Wet scratch resistance [N] |
| 1 | H-1 | 100 | 3.7 | 2.6 | 100 | 100 | 3.5 | 5.0 |
| 2 | H-5 | 100 | 3.9 | 2.2 | 100 | 100 | 3.6 | 4.5 |
| 3 | C-2 | 40 | 5–6 | <2.0 | 40 | 100 | 4.1 | <2.0 |

TABLE 3

| Compound 0.08 mole/100 g gelatin | Values after storage for 30 days/22° C. in the absence of moisture | | | Storage for 3 days at 57° C./ 34% rel. humidity | | |
|---|---|---|---|---|---|---|
| | Duration of resistance to boiling water (mins.) | Swelling factor | Wet scratch resistance B/W developer, 38° C. | Wrinkled grain | Swelling factor | Wet scratch resistance B/W developer, 38° C. |
| H 12 | 7 | 3.0 | 2.0 | — | 2.9 | 2.5 |
| H 13 | 6 | 2.8 | 2.0 | — | 3.0 | 2.5 |
| H 14 | 4 | 3.1 | 1.5 | — | 3.2 | 2.5 |
| H 15 | 6 | 3.5 | 1.5 | — | 3.5 | 3.5 |
| H 5 | 10 | 2.6 | 3.0 | — | 2.9 | 5.0 |
| H 18 | 10 | 3.3 | 3.5 | — | 3.6 | 5.0 |
| H 8 | | 4.4 | 1.0 | — | 4.0 | 2.5 |
| H 16 | | 5.4 | 1.5 | — | 3.0 | 3.5 |
| H 17 | | 4.0 | 3.5 | — | 2.5 | 5.5 |

It can be seen from Table 3 that the compounds according to the invention show no wrinkled grain, even where their hardening effect is slightly poorer, and that, in every case, a completely uniform hardening effect is obtained in every layer.

We claim:

1. A photosensitive silver halide photographic recording material comprising at least one hardened gelatin-containing layer, characterized in that a water-soluble adduct of the following formula

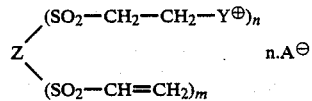

in which

Y is the residue of a tertiary amine,

Z corresponds to one of the following formulae

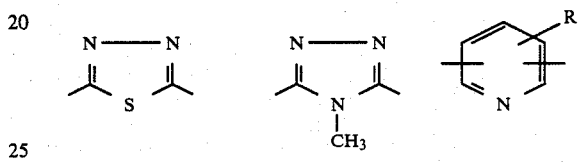

where R represents hydrogen, $C_1$–$C_4$ alkyl, phenyl or $C_1$–$C_4$ alkoxy $A^{\ominus}$ is an anion, n is an integer of $\geq 1$, m is an integer of $\geq 0$ and m+n is 2 is used as a hardener.

2. A photosensitive photographic recording material as claimed in claim 1, wherein from 0.01 to 15% by weight hardener, based on the dry weight of the gelatin, has been used.

3. A photosensitive photographic recording material as claimed in claim 1, wherein from 0.1 to 5% by weight hardener, based on the dry weight of the gelatin, has been used.

* * * * *